US006054447A

United States Patent [19]
Levine et al.

[11] Patent Number: 6,054,447
[45] Date of Patent: Apr. 25, 2000

[54] PROGESTERONE FOR TREATING OR REDUCING ISCHEMIA

[75] Inventors: Howard L. Levine, Oceanside; William J. Bologna, New York, both of N.Y.

[73] Assignee: Columbia Laboratories, Inc., Aventura, Fla.

[21] Appl. No.: 09/240,610

[22] Filed: Feb. 1, 1999

Related U.S. Application Data

[63] Continuation of application No. 08/743,153, Nov. 4, 1996, Pat. No. 5,985,861.

[51] Int. Cl.$^7$ .................................................. A61K 31/56
[52] U.S. Cl. ........................................ 514/177; 514/170
[58] Field of Search ..................................... 514/177, 170

[56] References Cited

U.S. PATENT DOCUMENTS 5,543,150   8/1996   Bologna et al. ......................... 424/430

OTHER PUBLICATIONS

Sarrell, Phillip M., "How Progestins Compromise the Cardioprotective Effects of Estrogen," *Menopause: The Journal of the North American Menopause Society*, vol. 2, No. 4, 1995, pp. 187–190.

Sullivan, Jay M. et al., "Progestin Enhances Vasoconstrictor Responses in Postmenopausal Women Receiving Estrogen Replacement Therapy," *Menopause: The Journal of the North American Menopause Society*, vol. 2, No. 4, 1995, pp. 193–199.

Williams, J. Koudy et al., "Effects of Hormone Replacement Therapy on Reactivity of Atherosclerotic Coronary Arteries in Cynomolgus Monkeys," *Journal of the American College of Cardiology*, vol. 24, No. 7, Dec. 1994, pp. 1757–1761.

Perrot–Applanat, M. et al., "Progesterone Receptor Expression in Human Saphenous Veins," *Circulation*, vol. 92, No. 10, Nov. 15, 1995, pp. 2975–2983.

Stumpf, W.E., Steroid hormones and the cardiovascular system: Direct actions of estradiol, progesterone, testosterone, gluco– and mineralcorticoids, and soltriol [vitamin D] on central nervous regulatory and peripheral tissues, *Experimentia*, vol. 46, No. 1, Jan. 15, 1990, pp. 13–25.

Ingegno, Michael D. et al., "Progesterone Receptors in the Human Heart and Great Vessels," *Laboratory Investigation*, vol. 59, No. 3, Sep. 1988, pp. 353–356.

Perrot–Applanat, M. et al., "Immunocytochemical Demonstration of Estrogen and Progesterone Receptors in Muscle Cells of Uterine Arteries in Rabbits and Humans," *Endocrinology*, vol. 123, No. 3, Sep. 1988, pp. 1511–1519.

Brucket, Eric et al., "Estrogens and Progestins in Postmenopausal Woman: Influence on Lipid Parameters and Cardiovascular Risk," *Hormone Research*, vol. 43, pp. 100–103.

Sullivan, Jay M. et al., "Considerations for contraception in women with cardiovascular disorders," *American Journal of Obstetrics and Gynecology*, vol. 168, No. 6, Part 2, Jun. 1993, pp. 2006–2011.

Sammour, M.B. et al., "Progesterone Therapy in Pregnancy Induced Hypertension–Therapeutic Value and Hormonal Profile," *Clinical and Experimental Hypertension: Part B, Hypertension in Pregnancy*, vol. B1, No. 4, 1982, pp. 455–478.

Castelo–Branco, Camil et al., "Postmenopausal Hormone Replacement Therapy with Low–Dose Medroxyprogesterone Acetate," *The Journal of Reproductive Medicine*, vol. 40, No. 4, Apr. 1995, pp. 305–311.

Kafonek, Stephanie D., "Postmenopausal Hormone Replacement Therapy and Cardiovascular Risk Reduction," *Drugs Supplement: Treatment of Lipoprotein Disorders in Women*, vol. 47, Supplement 2, 1994, pp. 16–24.

Giraud, George D. et al., "Effects of estrogen and progestin on aortic size and compliance in postmenopausal women," *American Journal of Obstetrics and Gynecology*, vol. 174, No. 6, Jun. 1996, pp. 1708–1718.

Barberis, Massimo C.P. et al., "Immunocytochemical Detection of Progesterone Receptors," *Chest*, vol. 107, No. 3, Mar. 1995, pp. 869–872.

Gaspard, U. et al., "Impact Metabolique des Oestroprogestatifs Actuels et Repercussions Cardiovaculaires," *Bulletin et Memoires de l'Academie Royale de Medecine de Belgique*, vol. 146, Nos. 8–10, 1991, pp. 334–342, at English summary on p. 341.

Horwitz, Kathryn B. et al., "Canine Vascular Tissues are Targets for Androgens, Estrogens, Progestins and Glucocorticords," *The Journal of Clinical Investigation*, vol. 69, Apr. 1982, pp. 750–758.

Gambrell, Jr., R.. Don, "Use of Progestogens in Postmenopausal Woman," *International Journal of Fertility*, vol. 34, No. 5, Sep./Oct. 1989, pp. 315–321.

Abstract, Section CH, Week 8523, Derwent Publications Ltd., London, GB; AN 85–139803 XP002055336 & SU 1 124 906 (Ivan Medicine Inst.), Nov. 23, 1984.

Giuseppe, Rosano et al., Medroxyprogesterone but not natural progesterone reverses the beneficial effect of estradiol 17 beta upon exercise–induced myocardial ischemia, *Circulation* (Supplement), vol. 94, No. 8 p. 18 (Oct. 15, 1996).

Rosano et al. Maturitas 27 (Suppl.), Nov. 3–7, 1996.

Jiang et al, Eu. J. Pharmacol:, vol. 211, pp. 163–167, 1992.

Fahraeus et al, Eu. J. Clinical Investig, vol. 13, pp. 447–453, 1983.

Omar et al, J. Clinical Endocrin. and Metab., vol. 80(2), pp. 370–373, 1995.

Belfort et al, Am. J. Obstet. Gynecol. vol. 174(1) Part 1, pp. 246–253, Jan. 1996.

*Primary Examiner*—Rebecca Cook
*Attorney, Agent, or Firm*—Fulbright & Jaworski L.L.P.

[57] ABSTRACT

The present invention provides a method of treating or reducing ischemia or incidence of cardiovascular events by administering progesterone. Progesterone, unlike synthetic progestins, has been demonstrated to supplement, rather than to decrease, the beneficial effects of estrogen therapy on myocardial ischemia in females.

18 Claims, No Drawings

PROGESTERONE FOR TREATING OR REDUCING ISCHEMIA

This is a continuation of application Ser. No. 08/743,153, filed Nov. 4, 1996 now U.S. Pat. No. 5,985,861.

FIELD OF THE INVENTION

This invention relates to the administration of progesterone for the purpose of treating or reducing ischemia or incidence of cardiovascular events.

BACKGROUND

Ischemia is a decrease in the blood supply to a body organ, tissue or part caused by constriction or obstruction of the blood vessels. Ischemia is often linked to coronary artery disease, cardiovascular events, angina, headaches or other vascular symptoms.

Myocardial ischemia is a particularly prevalent problem for menopausal females. Estradiol 17β (E2) has anti-ischemic properties and has been suggested for primary and secondary prevention of coronary artery disease in menopausal females. However, a large proportion of menopausal women need adjunctive therapy with progestins, which include progesterone and the synthetic progestins, in order to reduce the occurrence of uterine malignancy. The synthetic progestins, unlike progesterone, normally can be effectively administered orally, and so have been the predominant choice over progesterone itself, which is minimally active when administered orally. One major problem with co-treatment using synthetic progestins, however, is that synthetic progestins, such as medroxyprogesterone acetate (MPA), tend to reverse some or all of the beneficial effects of estrogen on myocardial ischemia. Use of progestins in women with cardiovascular problems has often been avoided due to negative effects associated with these drugs. MPA is one of the most prescribed and tested progestins in hormone replacement therapy.

Use of a progestin in hormone replacement therapy that actually supplements, rather than adversely interferes with, estrogen replacement therapy for women with ischemia is therefore of particular interest. Unlike synthetic progestins, administration of progesterone itself provides this unexpected benefit.

DESCRIPTION OF RELATED ART

Estrogen replacement therapy (ERT) in post-menopausal women inhibits the development of atherosclerosis and reduces the frequency of cardiovascular events. At the same time, though, prolonged, unopposed ERT has the potential to also cause hyperplastic and perhaps carcinomatous effects. Progestins have long been used to protect the endometrium from these deleterious effects of ERT. However, synthetic progestins are well known to act as vasoconstrictive agents to reduce the cardioprotective effects of estrogen replacement therapy on post-menopausal women. This is a main concern about progestin administration. See, e.g., Sarrel, P. M., *Menopause: The Journal of the North American Menopause Society,* 2(4):187–90 (1995) ("Perhaps the safest way to gain from the benefits of ERT is to use a nonsystemic progestin that acts only in the uterine lining"); Sullivan, J. M., et al., *Menopause: The Journal of the North American Menopause Society,* 2(4):193–99 (1995).

MPA was shown to diminish the beneficial effect of conjugated equine estrogens on vasomotion of diet-induced atherosclerotic coronary arteries in monkeys. Williams, J. K., et al., *Journal of the American College of Cardiology,* 24(7): 1757–61 (1994).

SUMMARY OF THE INVENTION

The present invention comprises the administration of progesterone to treat or reduce ischemia or incidence of cardiovascular events, or to treat coronary artery disease. Unlike synthetic progestins, progesterone is demonstrated to reduce ischemia. Thus, for example, progesterone, but not the synthetic progestins, can be used in hormone replacement therapy with positive effects, rather than negative effects, on ischemia treatment.

DETAILED DESCRIPTION OF THE INVENTION

Use of progesterone as taught by the instant invention is particularly useful, for example, with patients undergoing estrogen replacement therapy. Estrogen replacement therapy for menopausal patients with coronary artery disease is often accompanied by adjunctive administration of progestins, to counter any estrogen-induced tendency to promote uterine malignancy. However, synthetic progestins, which are normally effective when administered orally (unlike progesterone), tend to at least partially reverse the beneficial results demonstrated by chronic estrogen therapy on myocardial ischemia. Accordingly, the use of progestins in women with cardiovascular problems has often been avoided.

Progesterone, however, has now been demonstrated to maintain or reduce, rather than to increase, ischemia. For example, in combination with estrogen therapy, progesterone is demonstrated to further reduce myocardial ischemia.

One specific example detailed below reports a recent study which administered progesterone to menopausal women undergoing estrogen therapy for treatment of effort-induced myocardial ischemia. The progesterone reduced ischemia above and beyond the treatment benefits achieved with estrogen alone.

As will be apparent to those skilled in the art, the mode of administration, as well as the target treatment population, can easily be varied to achieve positive results in a far broader spectrum. There is no indication whatsoever that the mode of administration or the subject population should be expected to affect the ultimate efficacy of progesterone used to treat or reduce ischemia. Various routes of administration, as well as specific dosing, can be routinely evaluated through traditional dose ranging studies to easily identify appropriate dosing regimens for specific patients or population.

The specific drug delivery formulation chosen and used in the Example below comprises a cross-linked polycarboxylic acid polymer formulation, generally described in the U.S. Pat. No. 4,615,697 to Robinson (hereinafter "the '697 patent"), which is incorporated herein by reference. Such a formulation could be prepared with progesterone, for administration to mucosal surfaces, particularly in a body cavity, as further described in the U.S. Pat. No. 5,543,150 to Bologna and Levine (hereinafter "the '150 patent"), which is incorporated herein by reference.

In general, at least about eighty percent of the monomers of the polymer in such a formulation should contain at least one carboxyl functionality. The cross-linking agent should be present at such an amount as to provide enough bioadhesion to allow the system to remain attached to the target epithelial surfaces for a sufficient time to allow the desired dosing to take place.

For vaginal administration, such as in the Example below, preferably the formulation remains attached to the epithelial surfaces for a period of at least about twenty-four to forty-eight hours. Such results may be measured clinically over various periods of time, by testing samples of the vaginal vault for pH reduction due to the continued presence of the polymer. This level of bioadhesion is usually attained when the cross-linking agent is present at about 0.1 to 6.0 weight percent of the polymer, with about 1.0 to 2.0 weight percent being preferred, as long as the appropriate level of bioadhesion results. Bioadhesion can also be measured by commercially available surface tensiometers utilized to measure adhesive strength.

As discussed in the '150 patent, the polymer formulation can be adjusted to control the release rate of the progesterone, e.g., by varying the amount of cross-linking agent in the polymer. Suitable cross-linking agents include divinyl glycol, divinylbenzene, N,N-diallylacrylamide, 3,4-dihydroxy-1,5-hexadiene, 2,5-dimethyl-1,5-hexadiene and similar agents.

A preferred polymer for use in such a formulation is Polycarbophil, U.S.P., which is commercially available from B.F. Goodrich Speciality Polymers of Cleveland, Ohio under the trade name NOVEON®-AA1. The United States Pharmacopeia, 1995 edition, United States Pharmacopeial Convention, Inc., Rockville, Md., at pages 1240–41, indicates that polycarbophil is a polyacrylic acid, cross-linked with divinyl glycol.

Other useful bioadhesive polymers that may be used in such a drug delivery system formulation are mentioned in the '697 patent. For example, these include polyacrylic acid polymers cross-linked with, for example, 3,4-dihydroxy-1, 5-hexadiene, and polymethacrylic acid polymers cross-linked with, for example, divinyl benzene.

Typically, these polymers would not be used in their salt form, because this would decrease their bioadhesive capability. Such bioadhesive polymers may be prepared by conventional free radical polymerization techniques utilizing initiators such as benzoyl peroxide, azobisisobutyronitrile, and the like. Exemplary preparations of useful bioadhesives are provided in the '697 patent.

Additionally, the additives taught in the '697 patent may be mixed in with the cross-linked polymer in the formulation for maximum or desired efficacy of the delivery system or for the comfort of the patient. Such additives include, for example, lubricants, plasticizing agents, preservatives, gel formers, binders, vehicles, coloring agents, taste and/or odor controlling agents, humectants, viscosity controlling agents, pH-adjusting agents and similar agents.

COL-1620, the specific preparation used in the study discussed in the Example below, consisted of the following:

| INGREDIENT | AMOUNT (% w/v) |
|---|---|
| Progesterone | 8.00 |
| Sorbic Acid | 0.08 |
| Carbomer 934P | 1.00 |
| Polycarbophil | 2.00 |
| Glycerin | 12.90 |
| Mineral Oil | 4.20 |
| Hydrogenated Palm Oil Glyceride | 1.00 |
| Purified Water | (remainder) |

Sorbic acid is a preservative, which may be substituted by any other approved preservative, such as benzoic acid or propionic acid.

Carbomer 934P is a gel former, which may be substituted by other gel formers including, but not limited to, Carbomer 974, Carbomer 980, methyl cellulose or propyl cellulose.

Glycerin is a humectant; alternative humectants include, for example, propylene glycol or dipropylene glycol.

Mineral oil and hydrogenated palm-oil glyceride are lubricating agents; alternatives include, for example, any mineral oil or vegetable oil, such as canola oil, palm oil or light mineral oil.

Preparation of the formulation involves hydration of the polymers, separate mixing of water-soluble ingredients (the "polymer phase") and oil-soluble ingredients (the "oil phase"), heating and mixing of the two phases, and homogenization of the mixture. All ingredients in COL-1620 are well known and readily available from suppliers known in the industry.

The polymer phase may generally be prepared by dissolving the sorbic acid in purified water (along with an excess volume of about 3% of the intended volume of water, to account for evaporation losses), preferably at 75–78° C. The solution is cooled, generally to room temperature, and the polycarbophil and Carbomer 934P are added. The polymers are hydrated by mixing for several hours, generally about 2–3 hours until a uniform, smooth, lump-free gel-like polymer mixture is obtained. When the polymers are completely hydrated, the progesterone is added and mixed in, until a homogeneous suspension is obtained.

The oil phase is generally prepared by melting together the hydrogenated palm oil glyceride, glycerin and mineral oil. The mixture is cooled to about 60° C., while the polymer phase is warmed to about the same temperature.

The oil phase is then added to the polymer phase, and the two phases are mixed thoroughly, producing a uniform, creamy white product with a pH generally of about 3. When the mixture has cooled, it is de-aerated. The resulting product is aseptic, because of the nature of the preparation as well as the pH and the presence of preservatives.

As will be apparent to those skilled in the art, the composition of the formulation can be varied to affect certain properties of the formulation. For example, the concentration of the bioadhesive polymer can be adjusted to provide greater or lesser bioadhesion. The viscosity of the gel can be varied by varying the pH or by changing the concentration of the polymer or gel former. The relative concentrations of the oils compared to the water can be varied to modulate the release rate of the progesterone from the drug delivery system. The pH can also be varied as appropriate or to affect the release rate or bioadhesiveness of the formulation.

EXAMPLE

In a recent cross-over study, menopausal woman, suffering from angina pectoris, received twice-a-week treatment with generic Estradiol 17β: Estradiol 1 mg orally per day for 18 days, and then with Estradiol 2 mg orally per day for the duration of the study. At day 29, the patients received, according to a random list, either: (1) COL-1620, formulated as discussed above, a vaginal application of progesterone at a dose of 90 mg per application for administration every other day during 12 consecutive days (6 applications) along with Medroxyprogesterone acetate placebo tablets to be taken twice daily (24 tablets total); or (2) Medroxyprogesterone acetate 5 mg. tablets to be taken twice daily (24 tablets total), along with a placebo vaginal progesterone application for administration every other day for 12 consecutive days (6 applications). Each of the two patient groups then received the alternate treatment set—16 days of Estradiol 2 mg orally per day without a progestin, followed by 12 days with both the Estradiol and the progesterone/MPA treatment, with corresponding placebo, that they did not receive in the first part of the study.

The subjects were women, between the ages of 45 and 70 years, who were post-menopausal and with an intact vagina. The women suffered from angina pectoris, as confirmed by demonstrating a positive exercise test using the standard Bruce protocol, with one modification—before beginning the Bruce protocol activity, the patients walked for three minutes at a speed of 1.7 miles per hour. Patients with unstable angina were excluded or withdrawn from the study.

All patients underwent repeated exercise testing on days 28 (the first leg of Estrogen alone), 35 (Estrogen plus progesterone or MPA), 56 (second leg with Estrogen alone) and 63 (Estrogen plus MPA or progesterone). Exercise testing was done at about the same hour of the day, using the Bruce protocol as discussed above. Nitrates other than sublingual nitroglycerin were withdrawn one day before the study; calcium channel blocking and $\beta$-adrenergic blocking agents were withdrawn 4 and 5 days beforehand, respectively. At least 6 hours elapsed between use of sublingual nitroglycerin and each exercise test.

A 12-lead electrocardiogram was obtained at rest, every minute during the exercise test, at the onset of 1 mm of ST segment depression, at peak exercise and every minute during recovery. Leads V2, V5 and II were continuously monitored and a complete 12-lead electrocardiogram obtained at the end of each stage, at the onset of 1 mm planar ST segment depression and at peak exercise. Systolic and diastolic blood pressure were measured at rest and monitored every 3 minutes during exercise and recovery.

A positive response in the EKG was defined in the study protocol as a horizontal or downsloping ST segment depression of at least 1 mm at 60 ms after the J point occurring at least in 6 consecutive complexes. Otherwise, the patient was determined to have a "negative response" in that leg of the testing. The exercise test was concluded at the point of physical exhaustion, ST segment depression greater than 3 mm, severe angina, severe dyspnoea, complex arrhythmia or a decline in systolic blood pressure greater than 20 mm Hg. Total exercise time, time to myocardial ischemia, duration of EKG ischemic changes, heart rate, blood pressure at the onset of 1 mm ST segment depression, maximal ST depression and the time of development of angina during exercise was recorded.

The ST segment, 60 ms after the J point, was evaluated after signal averaging using a computer-assisted system in all 12 leads. The lead showing the greatest ST segment depression in the pre-treatment exercise test was selected for analysis.

Patients experiencing a serious adverse reaction were immediately withdrawn from the study. Accordingly, of the 18 patients to enter the treatment phase of the study, 2 patients were withdrawn due to unstable angina during the MPA phase. One additional patient, patient #22, developed unstable angina during the MPA phase, but it was the last study interval for that patient and the development occurred after the final exercise testing on day 63.

The primary analysis of the results focused on time to 1 mm ST segment depression. Effect of treatment was evaluated only in the absence of a carry-over effect. The use of run-in and wash-out estrogen periods allowed testing of first and second carry-over effects. The first order carry-over represents any difference between groups of the second base line means. The second order carry-over represents any treatment by period interaction, whether due to carry-over difference or not. Otherwise, the treatment effect was analyzed only for the first period as parallel groups adjusted on baseline (run-in period). Two-way analysis of variance (ANOVA) was used, one factor including the treatments effect and the other the subject effect.

The results were as follows:

TABLES 1–4. CRINONE VS. MPA IN ESTROGENIZED WOMEN WITH CHRONIC STABLE ANGINA—TIME TO 1 MM OF ST SEGMENT DEPRESSION (in seconds) WOMEN WHO RECEIVED MPA FIRST

TABLE 1

E2 VS. TIME 0 ($T_0$)

| | $T_0$ Time to ST Dep. | E2 Time to ST Dep. | | |
|---|---|---|---|---|
| Pt | Untreated | E2 | E2 − $T_0$ | % |
| 2 | 180 | 420 | 240 | 133% |
| 3 | 360 | 240 | −120 | −33% |
| 21 | 120 | 198 | 78 | 65% |
| 23 | 250 | 350 | 100 | 40% |
| 26 | 178 | N | (+) | (+) |
| 27 | 420 | 360 | −60 | −14% |
| 29 | 197 | N | (+) | (+) |
| 32 | 204 | 265 | 61 | 30% |

TABLE 2

E2 + MPA VS. E2

E2 + MPA time to ST Depression

| E2 + MPA | E2 + MPA − E2 | % |
|---|---|---|
| 650 | 230 | 55% |
| 360 | 120 | 50% |
| 163 | −35 | −18% |
| 246 | −104 | −30% |
| 358 | (−) | (−) |
| 420 | 60 | 17% |
| 180 | (−) | (−) |
| 223 | −42 | −16% |

TABLE 3

E2 VS. E2 + MPA

E2 Time to ST Depression

| Pt | E2 | E2 − E2 + MP | % |
|---|---|---|---|
| 2 | 300 | −350 | −54% |
| 3 | 420 | 60 | 14% |
| 21 | 235 | 72 | 44% |
| 23 | 293 | 47 | 19% |
| 26 | 360 | 2 | 1% |
| 27 | 420 | 0 | 0% |
| 29 | 460 | 280 | 156% |
| 32 | 170 | −53 | −24% |

TABLE 4

E2 + P VS. E2

E2 + P Time to ST Depression

| E2 + P | E2 + P − E2 | % |
|---|---|---|
| 698 | 398 | 133% |
| 480 | 60 | 14% |
| 254 | 19 | 8% |
| 309 | 16 | 5% |
| 413 | 53 | 15% |
| 540 | 120 | 29% |
| 471 | 11 | 2% |
| 360 | 190 | 112% |

N = Negative Test
(+) = lengthening of time (no quantity: current test was negative)
(−) = shortening of time (no quantity: prior test was negative)
n.c. = no change (no quantity: both prior and current tests were negative)

TABLES 5–8. CRINONE VS. MPA IN ESTROGENIZED WOMEN WITH CHRONIC STABLE ANGINA—TIME TO 1 MM OF ST SEGMENT DEPRESSION (in seconds) WOMEN WHO RECEIVED P FIRST

TABLE 5

E2 VS. TIME 0 ($T_0$)

| Pt | $T_0$ Time to ST Dep. Untreated | E2 Time to ST Dep. E2 | E2 − $T_0$ | % |
|---|---|---|---|---|
| 1 | 546 | 758 | 212 | 39% |
| 22 | 80 | N | (+) | (+) |
| 24 | 180 | N | (+) | (+) |
| 25 | 243 | N | (+) | (+) |
| 28 | 600 | N | (+) | (+) |
| 30 | 176 | 227 | 49 | 28% |
| 31 | 184 | 180 | −4 | −2% |
| 34 | 180 | 365 | 185 | 103% |

TABLE 6

E2 + P VS. E2

E2 + P Time to ST Depression

| E2 + P | E2 + P − E2 | % |
|---|---|---|
| 780 | 22 | 3% |
| N | n.c. | n.c. |
| N | n.c. | n.c. |
| N | n.c. | n.c. |
| N | n.c. | n.c. |
| 415 | 188 | 83% |
| N | (+) | (+) |
| 377 | 12 | 3% |

TABLE 7

E2 VS. E2 + P

E2 Time to ST Depression

| Pt | E2 | E2 − E2 + MP | % |
|---|---|---|---|
| 1 | N | (+) | (+) |
| 22 | 125 | (−) | (−) |
| 24 | N | n.c. | n.c. |
| 25 | N | n.c. | n.c. |
| 28 | N | n.c. | n.c. |
| 30 | 358 | −57 | −14% |
| 31 | 120 | (−) | (−) |
| 34 | N | (+) | (+) |

TABLE 8

E2 + MPA VS. E2

E2 + MPA Time to ST Depression

| E2 + MPA | E2 + MPA − E2 | % |
|---|---|---|
| 480 | (−) | (−) |
| 75 | −50 | −40% |
| 180 | (−) | (−) |
| 180 | (−) | (−) |
| 360 | (−) | (−) |
| 358 | 0 | 0% |
| 180 | 60 | 50% |
| 360 | (−) | (−) |

N = Negative Test
(+) = lengthening of time (no quantity: current test was negative)
(−) = shortening of time (no quantity: prior test was negative)
n.c. = no change (no quantity: both prior and current tests were negative)

The mean time to ST depression for E-2 alone before E2+P was 348 seconds. The mean time to ST depression for E2+P was 416 seconds. This difference was statistically significant, with a p value of 0.03. As demonstrated in Tables 1–8 above, 12 of the test subjects demonstrated an improvement when E2+P was administered, as compared with E2. Each of the other four subjects demonstrated no quantifiable change, each having negative tests for both the E2+P and the prior E2 intervals of the study. In stark contrast, the E2+MPA administration resulted in eleven subjects exhibiting worse results compared to E2. Only four of the E2+MPA subjects exhibited an improvement; one subject demonstrated no change.

The study results demonstrate that administration of progesterone, unlike MPA, supplements, rather than decreases, beneficial effects of estrogen therapy on myocardial ischemia. These results support the conclusion that progesterone, unlike synthetic progestins, may be used to treat or reduce ischemia or incidence of cardiovascular events, or to treat coronary artery disease.

Any and all publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now having been fully described, it will be apparent to those skilled in the art that many variations and modifications can be made thereto without departing from the spirit or scope of the appended claims.

What is claimed is:

1. A method of treating or reducing myocardial ischemia comprising administering to a subject in need of such treatment or reduction an effective amount of progesterone.

2. The method according to claim 1 wherein the myocardial ischemia is effort-induced.

3. The method according to claim 1 wherein the progesterone is administered via a drug delivery system which comprises a cross-linked polycarboxylic acid polymer and progesterone.

4. The method according to claim 3 wherein the polymer is polycarbophil.

5. A method of treating or reducing angina pectoris comprising administering to a subject in need of such treatment or reduction an effective amount of progesterone.

6. The method according to claim 3 wherein the subject is a female and the drug delivery system is administered vaginally.

7. The method according to claim 6 wherein a total of about 90 mg of progesterone is administered over a two-day period.

8. The method according to claim 2 wherein the progesterone is administered via a drug delivery system which comprises a cross-linked polycarboxylic acid polymer and progesterone.

9. The method according to claim 8 wherein the subject is a female and the drug delivery system is administered vaginally.

10. The method according to claim 9 wherein a total of about 90 mg of progesterone is administered over a two-day period.

11. The method according to claim 5 wherein the progesterone is administered via a drug delivery system which comprises a cross-linked polycarboxylic acid polymer and progesterone.

12. The method according to claim 11 wherein the subject is a female and the drug delivery system is administered vaginally.

13. The method according to claim 12 wherein a total of about 90 mg of progesterone is administered over a two-day period.

14. The method according to claim 3 wherein about 90 mg of progesterone is administered every other day.

15. The method according to claim 4 wherein about 90 mg of progesterone is administered every other day.

16. The method according to claim 7 wherein about 90 mg of progesterone is administered every other day.

17. The method according to claim 10 wherein about 90 mg of progesterone is administered every other day.

18. The method according to claim 13 wherein about 90 mg of progesterone is administered every other day.

* * * * *